United States Patent
Okazaki et al.

(12) 
(10) Patent No.: US 6,508,013 B1
(45) Date of Patent: Jan. 21, 2003

(54) METHOD OF QUICKLY DRYING A FRESH SAMPLE AND METHOD OF PRESERVING A DRIED BODY

(75) Inventors: Chizuko Okazaki, Obihiro (JP); Naoki Mita, Ibaraki (JP)

(73) Assignee: National Institute of Advanced Industrial Science and Technology, Tsukuba (JP)

( * ) Notice: Subject to any disclaimer, the term of this patent is extended or adjusted under 35 U.S.C. 154(b) by 0 days.

(21) Appl. No.: 09/606,460

(22) Filed: Jun. 29, 2000

(30) Foreign Application Priority Data

Jul. 2, 1999 (JP) .......................................... 11-224373

(51) Int. Cl.$^7$ ................................................. F26B 3/34
(52) U.S. Cl. ......................................... 34/259; 219/762
(58) Field of Search ........................... 34/259, 345, 353, 34/355, 358, 388; 219/685, 762; 427/4

(56) References Cited

U.S. PATENT DOCUMENTS

| | | | |
|---|---|---|---|
| 3,645,766 A | * 2/1972 | Mazzucato et al. | ............ 427/4 |
| 3,861,053 A | * 1/1975 | Rovetti | ........................ 34/353 |
| 5,592,752 A | * 1/1997 | Fu. et al. | ....................... 34/388 |
| 5,948,311 A | * 9/1999 | Beecroft et al. | ............ 219/762 |
| 6,025,580 A | * 2/2000 | Yogi | ........................... 219/685 |
| 6,237,245 B1 | * 5/2001 | Lunan | .......................... 34/259 |

FOREIGN PATENT DOCUMENTS

| | | | |
|---|---|---|---|
| JP | 4-49202 | 2/1992 | |
| JP | 405155701 | * 6/1993 | ............. A01N/3/00 |
| JP | 408119801 | * 5/1996 | ............. A01N/3/00 |
| JP | 09067203 | * 3/1997 | ........... B01D/53/26 |
| JP | 401117686 | * 5/1998 | .............. A23F/3/06 |

* cited by examiner

Primary Examiner—Teresa Walberg
Assistant Examiner—Leonid Fastovsky
(74) Attorney, Agent, or Firm—Flynn, Thiel, Boutell & Tanis, P.C.

(57) ABSTRACT

There are provided a method of drying a fresh sample in a short period of time, a method of fabricating a pressed flower or specimen which retains a beautiful color, and a method of fabricating tea or herb tea which retains a natural beautiful color and scent. The method of quickly drying a fresh sample is characterized in comprising the steps of covering an outer surface of a fresh sample with a moisture absorbent porous flexible sheet, surrounding the periphery of the moisture absorbent porous flexible sheet with moisture absorbent granular bodies in an amount capable of absorbing all moisture contained in the fresh sample, bringing the outer surface of the fresh sample, the moisture absorbent porous flexible sheet and the moisture absorbent granular bodies into intimate contact with one another, and irradiating the fresh sample, the moisture absorbent porous flexible sheet and the moisture absorbent granular bodies with a microwave, then cooling them.

20 Claims, 2 Drawing Sheets

METHOD OF QUICKLY DRYING A FRESH SAMPLE AND METHOD OF PRESERVING A DRIED BODY

BACKGROUND OF THE INVENTION

1. Field of the Invention

The invention relates to a method of preparing a botanical specimen in a short period of time which is bright and beautiful in color while keeping an original color intrinsic in the plant by utilizing granular silica gels and a microwave irradiated by a microwave oven, and a method of quickly drying and a method of preserving plant capable of easily preparing at low cost so as to preserve beautiful color of the botanical specimen that are just prepared as the botanical specimen and which are hardly discolored while keeping a beautiful color intrinsic in the plant.

Further, the invention relates to a method of quickly drying a plant which is capable of utilizing a dried plant such as tea or the like.

2. Related Art

As a method of preparing a botanical specimen or pressed flowers, there are many methods utilizing a weight, a gel indirectly, a gel directly, ceramic boards, and far-infrared radiation. Each method comprises fundamentally placing moisture-absorbent members on both the upper and lower portions of the botanical specimen or either the upper or lower portion of the botanical specimen, and drying the plant. Lately, there is a method utilizing dielectric heating by a microwave oven. A method of fabricating pressed flowers is now described hereinafter with reference to the typical method of drying flowers utilizing a gel indirectly.

The method of fabricating pressed flowers with reference to the method of drying flowers utilizing gel indirectly comprises the steps of:

(1) placing a sponge for pressed flowers on a drying sheet for pressed flowers and placing rayon paper for pressed flowers on the sponge for pressed flowers.

(2) arranging fresh flowers which are subjected to pretreatment on the rayon paper for pressed flowers so as to be easily fabricated so that the pressed flowers do not overlap with one another;

(3) overlaying the rayon paper for pressed flowers, the sponge for pressed flowers and the drying sheet for pressed flowers in this order on the fresh flowers;

(4) allowing the fresh flowers, the sponge for pressed flowers, the rayon paper for pressed flowers which are set in the steps 1 to 3 to introduce a vinyl sheet for pressed flowers, sandwiching the vinyl sheet between two pressing bodies for pressed flowers, applying pressure to the two pressing bodies by a Velcro (registered trademark) to fasten the two pressing bodies;

(5) letting air out of the vinyl sheet and closing a chuck of the opening of the vinyl sheet;

(6) replacing the drying sheet for pressed flowers with another upon the elapse of one or two days;

(7) completing pressed flowers if the fresh flowers are dried upon the elapse of three to six days.

If the drying sheet is not frequently replaced with another, it is impossible to fabricate pressed flowers which are bright in color.

Further, Japanese Patent Laid-Open Publication No. 4-49202 discloses a method of fabricating pressed flowers by irradiating a microwave.

That is, this method of fabricating pressed flowers is characterized in providing a pair of laminated boards between a ceramic board and a moisture absorbent sheet while sandwiching porous buffer agents therebetween wherein the flowering plant is tightly held at the side of the moisture absorbent sheet of each laminated board, and the flowering plant is subjected to drying treatment by dielectric heating in such a state.

The main feature of this method resides in the utilization of far-infrared rays emitted by the ceramic board which is heated by dielectric heating, wherein moisture contained in the flowering plant is uniformly heated by dielectric heating caused by a high frequency or a microwave together with far-infrared rays, thereby evaporating moisture in the flowering plant as described in page 2, right upper column, line 14 to left lower column, line 1 of Japanese Patent Laid-Open Publication No. 4-492020.

However, this method has a drawback that it takes time until the ceramic board is heated, and also takes time until the moisture contained in the flowering plant is heated and evaporated because the far-infrared rays are heat rays, and hence the flowering plant is liable to discolor. Particularly, if the quantity of the flowering plant increases, moisture contained in the flowering plant increases inevitably, and the porous buffering agent is a sponge intended for buffering alone and it has no moisture absorbent properties, and hence it takes time until the moisture is evaporated, thereby causing a strong tendency of discoloration of the flowing plant and resulting in dried flowers which are not prepared well.

The inventor confirmed that the method of preparing pressed flowers by the combination of ceramic boards and a microwave oven is not suited for the preparation of dried body such as a beautiful pressed flowers.

Table 1 shows the result of a comparison between the method of the invention (present method), the method utilizing ceramic boards and a microwave oven and the method utilizing pressing boards.

TABLE 1

|  | present method | ceramic boards and a microwave oven | pressing boards |
| --- | --- | --- | --- |
| thin flowers | about 50 to 60 seconds | about 1½ to 2 minutes | about 1 to 2 days |
| slightly thin flowers | about 60 to 70 seconds | about 2 to 2½ minutes | about 2 to 3 days |
| flowers of middle thickness | about 70 to 80 seconds | about 2½ to 3 minutes | about 3 to 4 days |
| slightly thick flowers | about 80 to 90 seconds | about 3 to 3½ minutes | about 4 to 5 days |
| flowers of medium thickness | about 90 to 100 seconds | about 3½ to 4 minutes | about 5 to 6 days |

As evident from Table 1, since plants serving as a fresh sample can be quickly dried according to the method of the present invention, the inventor confirmed that the dried plant is bright in color, and if the dried plant is used as the specimen, it takes much time until the discoloration of the samples occurs compared with the conventional method.

As mentioned above, it takes about 1 to 6 days to prepare the botanical specimen by the method using drying sheets for pressed flowers, and it takes 7 to 10 hours by a method utilizing far-infrared rays for pressed flowers, and it takes one and a half minutes to 4 minutes by the method utilizing a combination of a microwave oven and ceramic boards.

Among moisture, oxygen and ultraviolet light which cause deterioration and the discoloration of the botanical specimen, a conventional method of preserving botanical specimen does not consider a counterplan for ultraviolet light although a counterplan for each of moisture and oxygen by intercepting the circulation of air is considered. Accordingly, if the botanical specimen is exhibited in a well-lighted room, the occurrence of the discoloration of the botanical specimen is differentiated depending on the kind of plant, for example. The discoloration of the botanical specimen occurs or starts about half a year later after the exhibition in the case of heating films, about one year later in the case of Japanese paper or films for pressed flowers, and about five years later in the case of the airtight frame.

In the case of a conventional preserving method to allow the pressed flowers to introduce in a frame, silica gels are stuck or fixed to the backside of a back board of the frame by an adhesive tape, then a doubled aluminum foil having the same size as the back board is stuck onto the silica gels. The sticking is effected in the manner that the adhesive is developed around the inner edge of the back board to a large extent not to provide a gap in the developed adhesive, then placing the aluminum foil on the adhesive, finally sticking both the back board and the aluminum foil using a straw or cloth to not allow air to remain between the back board and the aluminum foil.

Then, doubled unwoven cloths or doubled fabrics or cooking paper having the same size as the back board is overlaid on the front side of the back board, and they are stuck to each other only at the edges thereof.

The botanical specimen is placed on the back board at arbitrary desired positions which were subjected to a pretreatment as mentioned above using a pin set. After the botanical specimen is positioned or disposed on the back board, an adhesive is pasted on the entire edge of the cooking paper on which the botanical specimen is arranged without providing a gap in the pasted extended adhesive, then a glass board is placed on the botanical specimen which is disposed on the back board.

Finally, both the back board and the glass board between which the botanical specimen is sandwiched are stuck to each other by an aluminum tape so as to surround the side surfaces thereof so that the aluminum tape is not seen from the front when both the overlaid back board and the glass board are introduced into a frame at the edges thereof.

Although there is a method for fabricating pressed flowers utilizing the combination of an aluminum foil and a vacuum pack while the front surface of the glass board is coated with an ultraviolet-cut agent, and a method utilizing an ultraviolet intercepting heating film, implements and chemical agents used in these fabricating methods are not frequently put on the market, and are expensive to acquire, and hence these methods generally have hardly spread.

If the botanical specimen is sealed hermetically while introducing silica gels into the sealed botanical specimen and is kept in a dark place, it can be fairly prevented from deteriorating or discoloring, and hence it is sufficient as far as they are kept. However, if the botanical specimen is observed while it is exhibited in a museum or the like or enjoyed while it is watched, its value as a specimen is reduced by half if it is discolored one or two years later after it is exhibited.

Among technologies for rendering the botanical specimen to be hardly discolored, there is a method using a material such as a special resin solution and a method of producing a vacuum state and keeping the botanical specimen in such a vacuum state. However, there are drawbacks generally in these methods that the material is hardly obtained or costs are frequently high.

When preparing a botanical specimen which is bright in color, it is generally said that moisture in the plant needs to be absorbed and dried as quickly as possible.

The invention relates to a method of preparing pressed flowers and a specimen retaining a beautiful color therein by drying a fresh sample in a short time, and also a method of preparing tea or herb tea retaining beautiful natural colors and scents therein.

Further, the invention relates to a method of quickly drying a fresh sample by irradiating moisture in the fresh sample with a microwave for resonating only molecules of water to heat them, evaporating the thus generated vapor as quickly as possible so that colors or scents intrinsic in original fresh sample remain.

In the case of a method of fabricating a botanical specimen such as a method utilizing drying sheets for pressed flowers, a method utilizing far-infrared rays for pressed flowers, a method utilizing ceramic boards for pressed flowers, it takes time for preparing such a botanical specimen. If the plant is buried in a container in which silica gels are contained and heated by a microwave oven, there is a possibility that the silica gels stick to the plant or the plant is twisted or discolored or moisture remains in the plant if many plants are buried in the container.

Further, implements used in these methods are sold as exclusive ones for pressed flowers, and hence they are expensive or frequently hard to obtain.

SUMMARY OF THE INVENTION

Ultraviolet-cut effect is generally subjected to a botanical specimen so as to prevent the botanical specimen from contacting with fresh air and ultraviolet rays, thereby rendering the botanical specimen bright in color as it is for a long period of time so that the discoloration of the botanical specimen is delayed.

The invention has been made to solve the problems of the conventional techniques, and it is an object of the invention to provide a method of fabricating the botanical specimen simply and in a short time period of time while the original color of the plant remains as it is, and a method of preserving the botanical specimen simply for a long period of time which is just prepared and bright in color while a beautiful color of the plant remains as it is, and also a method of fabricating and preserving the botanical specimen which is optimum in spreading by reviving and recycling a material close to himself or herself or a waste material or utilizing an article which is easily available and put on the market so as to reduce a fabricating cost and used in an educating site.

The inventor found the method of quickly drying a fresh sample by covering an outer surface of a fresh sample with a moisture absorbent porous flexible sheet, surrounding the periphery of the moisture absorbent porous flexible sheet by moisture absorbent granular bodies in an amount capable of absorbing all moisture contained in the fresh sample, bringing the outer surface of the fresh sample, the moisture absorbent porous flexible sheet and the moisture absorbent granular bodies into intimate contact with one another and irradiating the fresh sample, the moisture absorbent porous flexible sheet and the moisture absorbent granular bodies with microwaves.

The outer surfaces of the moisture absorbent granular bodies are covered with moisture absorbent porous bodies, for example, a corrugated cardboard box or the like for letting moisture absorbed by moisture absorbent granular bodies and/or moisture absorbent pulverulent bodies escape outside.

A dried sample obtained in the foregoing method can be utilized for drinking in the case of the dried sample being tea or an herb, or can be utilized as the specimen. It is possible to use an ultraviolet-cut film, means for intercepting oxygen, or a drying agent so as to prevent the dried body from being discolored.

It is very important to remove moisture contained in a fresh sample to dry the fresh sample as soon as possible in order to fabricate the botanical specimen which is bright in color in a short period of time.

To this end, it is considered that a silica gel sheet for pressed flowers and a drying sheet for pressed flowers are optimum as the moisture absorbent member. However, there are many cases of hardly obtaining such a moisture absorbent member, and it takes about one to six days to fabricate the botanical specimen merely utilizing these members.

Although there is a method utilizing a microwave oven, there is a likelihood that the plant becomes deformed or twisted.

After studying these problems comprehensively, the inventor has discovered that the fresh sample is wrapped and protected by a flexible porous sheet, and granular silica gels which are utilized as a drying agent for familiar foods serving as a moisture absorbent member are placed around the flexible porous sheet and a microwave oven is utilized.

It is considered that implements or chemical agents which are easily available and put on the market are selected and utilized so that even school children can fabricate a botanical specimen at a low cost so as to spread an ornamental botanical specimen widely.

The implements, the porous flexible sheet, moisture absorbent porous bodies and so forth used in the invention are put on the market and hence they are easily available.

It is possible to employ paper such as Japanese paper, tissue paper and paper for newsprint or cloth such as cotton as the porous flexible sheet.

Granular silica gels are typically used as moisture absorbent porous bodies. The granular silica gels which are put on the market for preserving a dried flower may be used or silica gels which are sealed for preserving foods such as confectionery may be collected. As the moisture absorbent porous bodies, there are a cork, a corrugated cardboard box, a perforated corrugated cardboard, and thick paper as the moisture absorbent porous bodies, and it is possible to introduce a drying agent in the corrugated cardboard box.

There are calcium chloride, calcium oxide (quicklime), silica gels and zeolite as the drying agent and a high polymer can be also used a the drying agent.

In addition to the foregoing goods, an ultraviolet-cut transparent film which is put on the market as office supplies, stationary or the like, ultraviolet-cut acryl resin solution for handcraft or a silicon paste or combination of these goods may be used.

A microwave oven for familiar use which is put on the market can be utilized as a microwave generating unit used in the invention. A large-sized microwave generating unit is used for fabricating dried bodies industrially in large quantity. Water in a fresh sample which is irradiated with a microwave becomes quickly hot and is changed to vapor. At this time, the thus produced vapor is absorbed instantaneously by the silica gels through the porous flexible sheet. The thus generated vapor is also instantaneously absorbed by moisture absorbent porous bodies, and it is quickly separated into a fresh sample and vapor, which is the main feature of the invention.

Accordingly, it should be avoided that moisture coming from the fresh sample is condensed and contacts the fresh sample. The thus generated vapor should be quickly absorbed so as to prevent the moisture coming from the fresh sample from condensing and contacting the fresh sample again.

Vapor which cannot be absorbed by silica gels around the porous flexible sheet can be absorbed by moisture absorbent porous bodies which are placed around the porous flexible sheet.

It is convenient to mix silica gels to which cobalt chloride is added into transparent silica gels so as to confirm as to whether moisture is absorbed by the silica gels or not. The silica gels to which cobalt chloride is added exhibits a blue color when dried but changes to pink when containing moisture so that the absorption of moisture can be determined at a glance. Paper and a cork are adapted for moisture absorbent porous bodies, and overlapped Japanese writing paper, a corrugated cardboard, a cork board and so forth, and the mixture of these materials with a drying agent are preferable as the moisture absorbent porous bodies.

The moisture absorbent porous bodies serve as a cushion when a weight is placed thereon.

When the production of vapor in a large quantity is expected, it is preferable that a corrugated cardboard is made in a box shape and silica gels or calcium chloride is introduced in the box-shaped corrugated cardboard. When handling many fresh samples, it is possible to use a corrugated cardboard box 30 having many perforations 31 and filled with drying agents 32 as shown in FIG. 3 as the moisture absorbent porous bodies.

If the moisture absorbent porous bodies do not work sufficiently, the corrugated cardboard box is filled with hot water or vapor so that the dried sample degrades in color, causing the discoloration or deterioration of color.

In conclusion, the quick drying method and the preserving method of the invention are as follows.

(1) A method of quickly drying a fresh sample of the first aspect of the invention is characterized in comprising the steps of covering an outer surface of a fresh sample with a moisture absorbent porous flexible sheet, surrounding the periphery of the moisture absorbent porous flexible sheet with moisture absorbent granular bodies in an amount capable of absorbing all moisture contained in the fresh sample, bringing the outer surface of the fresh sample, the moisture absorbent porous flexible sheet and the moisture absorbent granular bodies into intimate contact with one another, and irradiating the fresh sample, the moisture absorbent porous flexible sheet and the moisture absorbent granular bodies with microwaves, then cooling them.

(2) The method of quickly drying a fresh sample of the second aspect of the invention is characterized in that the outer surface of the fresh sample, the moisture absorbent porous flexible sheet and the moisture absorbent granular bodies of the first aspect of the invention are brought into contact with each other by applying a pressure thereto.

(3) The method of quickly drying a fresh sample of the third aspect of the invention is characterized in that the peripheries of the moisture absorbent granular bodies of the first aspect of the invention are covered with moisture absorbent porous bodies by way of the moisture absorbent porous flexible sheet.

(4) The method of quickly drying a fresh sample of the fourth aspect of the invention is characterized in that the moisture absorbent granular bodies of the first aspect of the invention are silica gels.

(5) The method of quickly drying a fresh sample of the fifth aspect of the invention is characterized in that the moisture absorbent porous bodies of the first aspect of the invention contain therein moisture absorbent pulverulent bodies and/or moisture absorbent granular bodies.

(6) The method of quickly drying a fresh sample of the sixth aspect of the invention is characterized in that the fresh sample of the first aspect of the invention is a plant.

(7) The method of quickly drying a fresh sample of the seventh aspect of the invention is characterized in that the plant of the first aspect of the invention is tea or an herb.

(8) The method of quickly drying a fresh sample of the eighth aspect of the invention is characterized in that the moisture absorbent porous flexible sheet of the first aspect of the invention is paper and the moisture absorbent porous bodies of the third aspect of the invention is a corrugated cardboard.

(9) The method of quickly drying a fresh sample of the ninth aspect of the invention is characterized in that the moisture absorbent porous bodies of the first aspect of the invention are formed of a corrugated cardboard box containing therein a drying agent such as a silica gel, calcium chloride and/or quicklime.

(10) The method of quickly drying a fresh sample of the tenth aspect of the invention is characterized in that the silica gels of the first aspect of the invention are discolored when they absorb moisture.

(11) The method of quickly drying a fresh sample of the eleventh aspect of the invention is characterized in that the discolored silica gels of the tenth aspect of the invention are recycled.

(12) A method of preserving a dried body according to the twelfth aspect of the invention obtained by the quick drying method as set forth in the first aspect of the invention is characterized in comprising the step of introducing the dried body into a bag made of an ultraviolet-cut transparent film as it is or together with at least one of a deoxidizing agent and a drying agent.

(13) The method of preserving a dried body of the thirteenth aspect of the invention is characterized in further comprising in the twelfth aspect of the invention the steps of temporary fixing the dried body onto a pasteboard, covering the entire dried body with a film, replacing a part of the film with an ultraviolet-cut transparent film, if need be, and hermetically preserving the dried body covered with the film.

(14) The method of preserving a dried body of the fourteenth aspect of the invention is characterized in the twelfth aspect of the invention, a front film is an ultraviolet transparent film.

(15) The method of preserving a dried body of the fifteenth aspect of the invention is characterized in the twelfth aspect of the invention, a back film is an adhesive film and further comprises an adhesive layer and a release layer.

(16) The method of preserving a dried body of the sixteenth aspect of the invention is characterized in the twelfth aspect of the invention, the dried body is preserved in a space in which a deoxidizing agent and/or a drying agent is contained.

(17) The method of preserving a dried body of the seventeenth aspect of the invention is characterized in the twelfth aspect of the invention, the dried body is fixed to a space which is sealed up by an ultraviolet-cut transparent resin at least on one side thereof, and a deoxidizing agent and/or a drying agent is introduced into the space.

PREFERRED EMBODIMENT OF THE INVENTION

A quick drying method which is actually carried out is now described in detail but the invention is not limited thereto.

Figure 1:
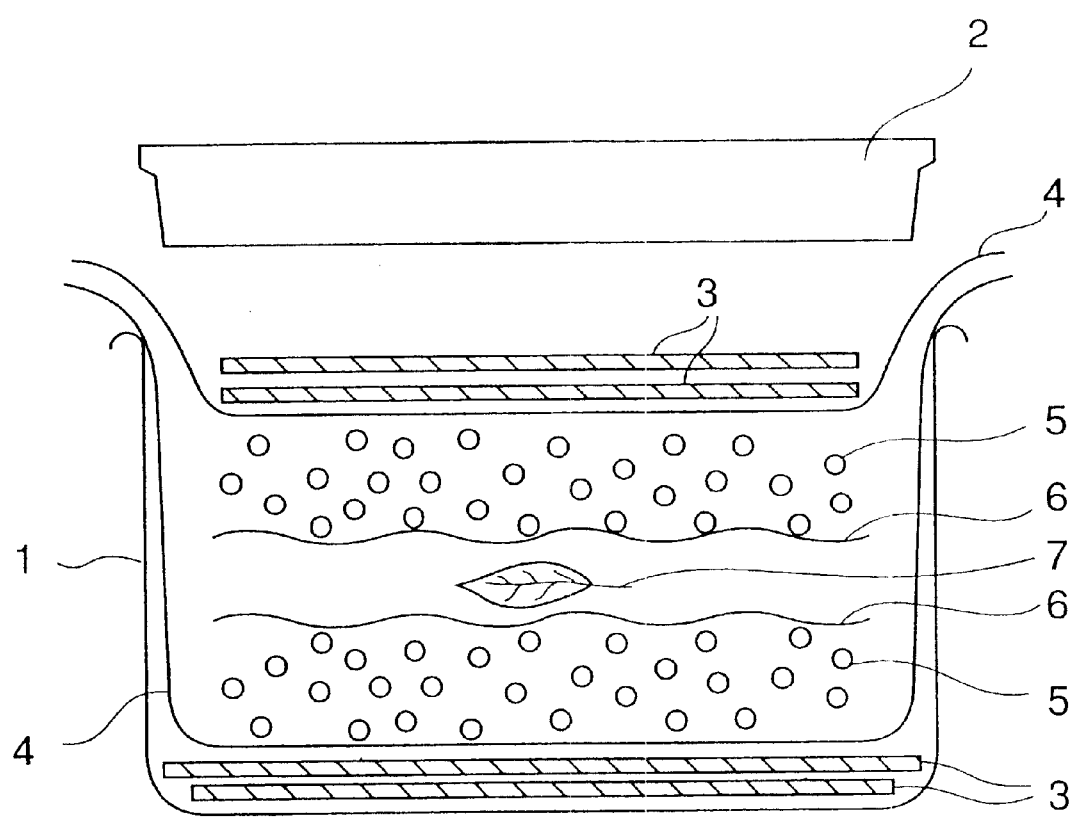
FIG. 1 is a sectional view of a drying apparatus used in the invention.
Figure 2:
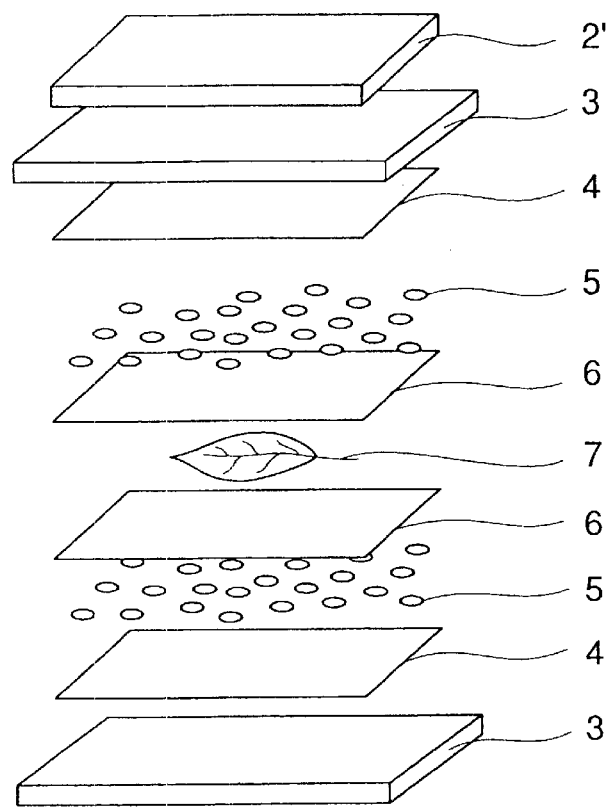
FIG. 2 is a view for explaining a drying method of the invention.
Figure 3:
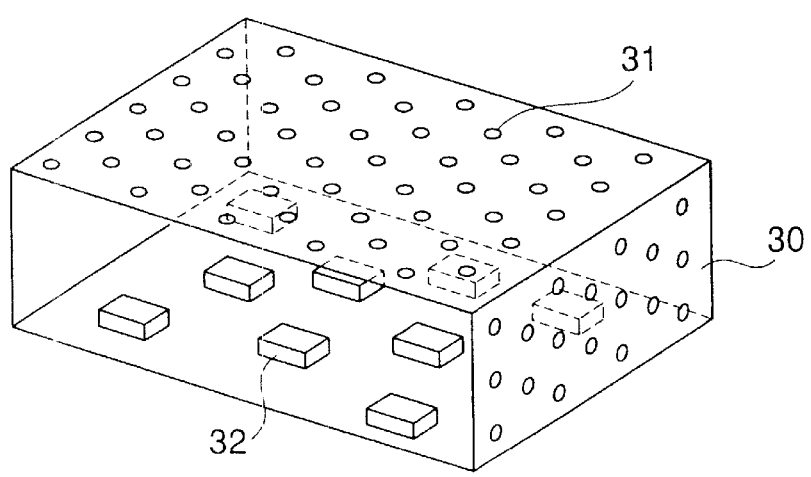
FIG. 3 is a perspective view of moisture absorbent porous bodies used in the invention.

A summary of the quick drying method is first described with reference to FIGS. 1 and 2.

A heat-resistant container 1 having a size to be introduced in a microwave oven is prepared, and corrugated cardboard or two cork boards 3 each having a thickness of about 2 mm are laid in the heat-resistant container 1 while they are overlaid on each other. Japanese writing paper or kitchen paper 4 is placed on the corrugated cardboard or two cork boards 3 each having a thickness of about 2 mm. Silica gels 5 are placed on the Japanese writing paper or kitchen paper 4 until they reach the height of about 0.6 to 1.5 cm, and several sheets of tissue paper 6 are overlaid on the Japanese writing paper or kitchen paper 4.

A plant 7 serving as a fresh sample, which is washed and shaped after it is subjected to pretreatment for removing extra stalk or leaves, is arranged on the tissue paper 6 to not overlap with another plant. In the reverse order to the foregoing order, the several sheets of tissue paper 6 are overlaid on the plant 7 serving as the fresh sample, then the silica gels 5 are placed on the tissue paper 6 until they reach the height of about 0.6 to 1.5 cm, and thereafter Japanese writing paper or kitchen paper 4 is overlaid on the silica gels 5 and finally the two corrugated cardboard or two cork boards 3 are overlaid on the Japanese writing paper or kitchen paper 4. Then, a lid 2 of the heat-resistant container 1 is turned inside out and fixed to the heat-resistant container 1 by rubber bands, or a weight such as a thick book or the like is placed on the opening of the heat-resistant container 1 for applying a light pressure to the plant serving as the fresh sample, thereafter, the heat-resistant container 1 with the lid 2 or weight is introduced in a microwave oven which is put on the market and finally the microwave is turned on to the heat-resistant container 1 with lid 2 or a weight.

EXAMPLE 1

There is described a case where a sample of one leaf of Trillium kamtschaticum Pall is prepared as a specimen by the quick drying method of the invention.

A heat-resistant container having a size of 20 cm×14.5 cm in length and breadth and a microwave oven of 600 W for familiar use which is put on the market are respectively used in the invention.

It is found that the quantity of silica gels to be used is not less than 250 g in total considering a thickness to cover the plant serving as the fresh sample after repeated trial and error although the silica gels are used to place above or under the plant serving as the fresh sample.

An excellent specimen is obtained by quickly drying the plant, namely, by heating the plant by the microwave oven for 60 seconds in the case that the entire weight of silica gels is 250 g, and for 50 seconds in the case that the entire weight of silica gels is 350 g. Further, an experiment has been effected in the case that the entire weight of silica gels is 400 g and in the case that the entire weight of silica gels is 450 g, respectively heating the plant for 50 seconds, resulting in obtaining an excellent specimen.

As a result of experiments it is conceived that the entire weight of silica gels is optimally 350 g.

If two kinds of silica gels which are different in shape, namely, granulated silica gels and granular silica gels are spread over the inside of the container in the thickness of 6 mm having the same capacity, it was possible to cover the sample with the granulated silica gels having the entire weight of 150 g, and possible to cover the container in the thickness of 8 mm with the granulated silica gels having the entire weight of 200 g. It was possible to cover the container in the thickness 5 mm with the granular silica gels having the entire weight of 150 g and possible to cover the container in the thickness of 7 mm with the granular silica gels having the entire weight of 200 g.

As the foregoing experiment, there occurs the difference in covering the container owing to the different shapes although the utilization time is the same even if the shapes of silica gels are different from each other. If the entire weight of the granular silica gels of 350 g is divided into two, the thickness of the container corresponding to 175 g of the granular silica gels ranges from 6 mm to 7 mm.

Although the heating time is varied depending on the size and thickness of the container and also depending on the thickness of the plant serving as a fresh sample, an experiment is effected in the same manner as Example 1 such that the plant serving as a fresh sample is laid on the container not to overlap one another, using the microwave oven for familiar use which has an output of 600 W and is put on the market, the silica gels having the entire weight of 350 g, and the container having the size of 2 cm×14.5 cm in length and breadth thereby obtaining the dried body which is bright in color.

The experiment condition and the result in the case of the ground pinks are respectively shown in Table 2.

TABLE 2

| name of plant | number of flowers | heating time (seconds) | number of flowers | heating time (seconds) | cooling time (minutes) |
| --- | --- | --- | --- | --- | --- |
| ground pink | 40 | 60 | 4 | 10 | 5 |
| pansy (including flower stalk) | 20 | 70 | 1 | 40 | 10 |

It is possible to adjust the experiment condition by reducing the heating time and cooling time in the case where the number of plants contained in the container is small or the plant has a small thickness.

The reason why the plant is heated by the microwave oven and then cooled to lower the temperature thereof is to prevent bare hands carrying the container from being burnt. Even if the same kind of plants are contained in the container, they are different in thickness and quantity of moisture depending on the part thereof so that the quantity of moisture which is different in the part of each plant serving as the fresh sample is adjusted by cooling the plant to complete the sample having a beautiful color tone.

The relation between heating time and cooling time is shown in Table 3.

TABLE 3

| | heating time by microwave oven (second) | cooling time (minutes) | weight of plant (g) |
| --- | --- | --- | --- |
| ground pink (4 flowers) | — | — | 0.08 |
| | 10 | — | 0.02 |
| | — | 5 | 0.01 |
| | — | 10 | 0.01 |
| German Iris (one leaf) | — | — | 1.66 |
| | 40 | — | 0.83 |
| | — | 5 | 0.33 |
| | — | 10 | 0.32 |
| | — | 10 | 0.32 |

As evident from Table 3, it was possible to fabricate a dried body which is bright in color in a short period of time beyond comparison with the conventional fabricating method.

However, red flowers of anthocyan is changed to blackish flowers because their acidity is changed when moisture is removed from the plant. The blackish color can be returned to the original color utilizing a red reduction treating agent which is put on the market although the blackish color can be developed to a good color by citric acid or tartaric acid.

Example for Drying Herbs

The quick drying method of the invention is applied to the case of drying the 20 flowers of lavenders and 20 flowers of camomiles, 80 leaves of thyme, 30 leaves of pineapple mint, 60 leaves of Japanese pepper.

Drying conditions in this case are shown in Table 4.

TABLE 4

| kinds of herbs | pretreatment | heating time by microwave oven (seconds) | cooling time (minutes) |
| --- | --- | --- | --- |
| lavender | — | 40 | 10 |
| camomile | — | 60 | 10 |
| thyme | yes | 20 | 10 |
| pineapple mint | yes | 20 | 10 |
| Japanese pepper | — | 50 | 10 |

The thyme and pineapple mint are put between a tissue paper and pressed by an iron at a medium temperature, then they are dried. Two flowers of camomile, two leaves of mint, and 36 flowers of lavenders are respectively used with a black tea in a tea bag made by Nittoh Kocha, and they are left for two minutes and compared with one another. The result of the comparison is shown in Table 5.

TABLE 5

| | | tea + fresh herb | tea + herb put on the market) | present invention |
| --- | --- | --- | --- | --- |
| camomile | scent | strong but grassy-smelling | mixed with dead leaf scent | weak scent but pure |
| | taste | bitter taste | black tea taste as it is | mellow taste |
| mint | scent | strong but grassy-smelling | scent of cake | weak scent but pure |
| | taste | bitter taste | taste of cake | mellow taste |
| lavender | scent | strong but grassy-smelling | strong dead leaf scent | weak scent but pure |

TABLE 5-continued

|  | tea + fresh herb | tea + herb put on the market) | present invention |
|---|---|---|---|
| taste | black tea taste as it is | bitter taste | mellow taste |

It is revealed that the colors and scents are excellent.

The method of drying herbs of the invention is compared with the conventional drying method, and the result of the comparison is shown in Table 6.

TABLE 6

| drying method | sterilization | time | scent | taste | tone of color | shape |
|---|---|---|---|---|---|---|
| natural drying | none | takes time | strong but scent of dry herb | mixed with taste of dry herb | blackish | bad |
| freeze drying | yes | takes little time | weak | clear | whitish | bad |
| present invention | yes | takes less time | pure scent | mellow taste | close to fresh tone | good |

Example of Method of Drying Tea Leaves

Ten pieces of young tea leaves heated by a microwave for 50 to 80 seconds in the same manner as the case of the herbs, and they are cooled for ten minutes. The result is shown in Table 7.

TABLE 7

| heating time by microwave oven (seconds) | tone of color | scent | taste |
|---|---|---|---|
| 50 | close to fresh tone | pure scent | mellow taste |
| 60 | close to fresh tone | pure scent | mellow taste |
| 70 | close to fresh tone | pure scent | mellow taste |
| 80 | close to fresh tone | pure scent | mellow taste |

It is revealed that young tea leaves are bright in color and highly fragrant, and the inventor drank the fabricated tea as powdered tea.

Example of Method of Preserving Botanical Specimen

The dried body fabricated by the quick drying method of the invention is introduced in an openable polyethylene bag or transparent bag through which air passes and which is put on the market. That is, an ultraviolet cut transparent film which is put on the market as office supplies is pasted on the entire surface of the polyethylene bag, then the dried body is introduced into this polyethylene bag.

If the size of the polyethylene bag is substantially the same as a post card, a silica gel of about 20 grams and iron powdered pocket heater (deoxidation agent) are introduced in the polyethylene bag, and the polyethylene bag is hermetically sealed while letting air out of the polyethylene bag, then the polyethylene bag is kept in a dark place.

Example of Method of Preserving Botanical Specimen as a Card

The dried body for forming a botanical specimen which is fabricated by the quick drying method of the invention is temporarily fixed to a pasteboard using silicon paste.

An adhesive ultraviolet-cut transparent film which is cut in a size larger than a pasteboard is pasted onto the surface where the dried body serves as a botanical specimen and air bubbles do not enter.

In the same manner as the front side, the adhesive ultraviolet-cut transparent film is pasted onto the backside of the dried body, then the adhesive ultraviolet-cut transparent films protruding from the front side of the pasteboard and that protruding from the backside of the pasteboard are stuck to each other and the extra stuck adhesive ultraviolet-cut transparent film is cut while the margin protruding from the front and back sides of the pasteboard remains by 2 to 3 mm.

Example of Method of Preserving Botanical Specimen as Frame

The dried body for forming the botanical specimen which is fabricated by the quick drying method of the invention is introduced in a frame, and an adhesive ultraviolet-cut transparent film is pasted on the surface of glass. It was possible to preserve the botanical specimen for a long period of time while a beautiful natural tone of color remains on the botanical specimen.

If the botanical specimen is intended to be preserved for a longer period of time, a deoxidation agent (iron powdered pocket heater) and a drying agent (silica gel) is stuck to the back surface of the card fabricated in the foregoing method by a double sided adhesive tape, then the card is temporarily fixed to a glass board of the frame onto which the adhesive ultraviolet-cut transparent film is stuck by a masking tape, and thereafter a silicon paste is applied thick into the masking tape. An aluminum foil for kitchen use is largely cut and the dull surface of the aluminum foil is pasted onto the silicon paste while letting air out of the aluminum foil, then the protruding part of the aluminum foil is cut by scissors after the silicon paste is completely pasted on the dull surface of the aluminum foil.

Further, an aluminum tape is stuck to the entire back surface to reinforce the card, and the circumference of the card is encircled by the aluminum tape to introduce in the frame, if need be.

Example of Method of Preserving Pasted Botanical Specimen

A craft wooden board is polished with sandpaper of 240 mesh to smooth the surface thereof, then a desired acrylic paint is applied onto the surface of the wooden board.

When the acrylic paint is dried, a silicon paste is pasted thinly onto the wooden board, then a botanical specimen is placed on the wooden board before the silicon paste is dried, thereafter the botanical specimen is lightly pressed by tissue paper.

When a silicon paste is dried, silicon paste is also pasted onto the surface of the botanical specimen, then fixative is sprayed on the silicon paste after the silicon paste is dried, thereafter the fixative is sprayed again on the silicon paste upon elapse of 2 to 3 minutes. An oil resin solution is applied to the botanical specimen once when the resin solution is dried, and an ultraviolet-cut aquatic acrylic resin solution is applied to the botanical specimen and the botanical specimen is waxed to complete the dried body. When the botanical specimen is intended to have a thick thickness, an acrylic resin is applied to the botanical specimen alternately vertically and laterally, and the drying and applying operations are repeated until a desired thickness is obtained. When the acrylic resin is applied to the botanical specimen until reaching the desired thickness, a finishing acrylic resin solution is applied to the botanical specimen, and the botanical specimen is polished with a silicon mixed was to complete the botanical specimen.

Example of Method of Preserving Botanical Specimen in Three Dimensions

Back paper of the adhesive ultraviolet-cut transparent film is pealed off, and the botanical specimen which is divided into each part is placed on the sticking surface of the adhesive ultraviolet-cut transparent film, and the adhesive ultraviolet-cut transparent film is lightly pressed by fingers, then another adhesive ultraviolet-cut transparent film is brought into contact with the plant while firmly pressing the extra margin of the adhesive ultraviolet-cut transparent film protruding from the contour of the plant along the contour of the plant by a modeler or the like, thereafter, it is cut by scissors by a size 1 to 2 mm larger than the botanical specimen. The botanical specimen fabricated every divided part thereof is stuck to a board or small pieces or the like by the silicon paste, then it is assembled so as to be viewed in three dimensions.

Example of Method of Preserving Botanical Specimen in Three Dimensions Using Deoxidization Agent Back paper of a double sized tape is pealed off, and a botanical specimen which is divided into each part is stuck to the adhesive surface of the double sided tape, then a silicon paste is stuck to the front surface of the botanical specimen.

When a silicon paste is dried, a fixative is sprayed, then the fixative is again sprayed 2 to 3 minutes later, thereafter an adhesive Japanese paper film is placed on the botanical specimen so as to be sandwiched between the adhesive surface of the double side tape and the botanical specimen. Another back paper of the double sided tape is pealed off, and Japanese paper film is placed on the back paper, then a cloth is applied to the botanical specimen while pressing with an iron at a medium temperature so as to stick the film onto the botanical specimen.

Craft fluid for pressed flowers is applied to the front surface of the botanical specimen and an ultraviolet-cut acrylic resin solution is applied to the botanical specimen after the craft fluid is dried, then wax is applied to the botanical specimen after the acrylic resin solution is applied.

The film is cut by scissors while remaining the edge of 1 to 2 mm, and the divided specimens are stuck to the film by silicon paste to complete the botanical specimen.

The thus obtained specimen is introduced in the frame, then iron powdered pocket heater and a drying agent which are respectively put on the market are introduced in the backside of the frame, thereafter the backside of the frame is sealed with an aluminum foil.

The thus obtained dried body by the quick drying method of the invention has an advantage that not only natural colors can be preserved for a long period of time but also a natural scent is emitted from the dried body and floats in the air, which has not been found in the conventional drying method. The dried body can be utilized as foods or specimens. Since the specimen can be easily fabricated, it is considered that this can be easily spread for school education and life education. Particularly, in the case of exhibition at an inspecting building, the dried body is invaluable as a specimen because it is not discolored compared with the dried body fabricated in the conventional method.

Further, since a botanical specimen can be easily fabricated at home and be preserved while maintaining a beautiful tone of color as it is, and also it can be utilized as an indoor ornament, it is possible to confirm a peripheral natural environment by his or her eyes by observing and collecting flowers and the like which bloom in a field so that every person can learn natural beauty close to him or her and is highly motivated and enlightened while enjoying the botanical specimen.

What is claimed is:

1. A method of quickly drying a fresh sample comprising the steps of;

covering an outer surface of the fresh sample with a moisture absorbent porous flexible sheet;

surrounding the periphery of the moisture absorbent porous flexible sheet with moisture absorbent granular bodies in an amount capable of absorbing all moisture contained in the fresh sample;

bringing the outer surface of the fresh sample, the moisture absorbent porous flexible sheet and the moisture absorbent granular bodies into intimate contact with one another; and irradiating the fresh sample, the moisture absorbent porous flexible sheet and the moisture absorbent granular bodies with a microwave, then cooling them.

2. The method of quickly drying a fresh sample according to claim 1, additionally comprising the steps of;

putting the fresh sample covered by the moisture absorbent porous flexible sheet and surrounded by the moisture absorbent granular body into a heat resistant container and covering the container with a part of the moisture absorbent porous flexible sheet extending out of the container; and irradiating the fresh sample, the moisture absorbent porous flexible sheet and the moisture absorbent granular bodies in the container with a microwave, then cooling them.

3. The method of quickly drying a fresh sample according to claim 1, wherein the moisture absorbent granular bodies are silica gels.

4. The method of quickly drying a fresh sample according to claim 2, wherein the moisture absorbent granular bodies are silica gels.

5. The method of quickly drying a fresh sample according to claim 3, wherein the silica gels discolor when they absorb moisture.

6. The method of quickly drying a fresh sample according to claim 5, wherein the discolored silica gels are recycled.

7. The method of quickly drying a fresh sample according to claim 1, wherein the peripheries of the moisture absorbent granular bodies are covered with moisture absorbent porous bodies by way of the moisture absorbent porous flexible sheet.

8. The method of quickly drying a fresh sample according to claim 7, wherein the moisture absorbent porous bodies contain moisture absorbent pulverulent bodies and/or moisture absorbent granular bodies.

9. The method of quickly drying a fresh sample according to claim 7, wherein the moisture absorbent porous body is a corrugated cardboard box containing therein a drying agent selected from the group consisting of silica gel, calcium chloride and quicklime.

10. The method of quickly drying a fresh sample according to claim 1, wherein the fresh sample is tea or an herb.

11. The method of quickly drying a fresh sample according to claim 7, wherein the fresh sample is tea or an herb.

12. The method of quickly drying a fresh sample according to claim 8, wherein the fresh sample is tea or an herb.

13. The method of quickly drying a fresh sample according to claim 1, additionally comprising the step of introducing the dried body into a bag made of an ultraviolet-cut transparent film alone or together with at least one of a deoxidizing agent and a drying agent.

14. The method of quickly drying a fresh sample according to claim 1, further comprising the steps of temporarily fixing the dried body onto a pasteboard, covering the entire dried body with a film, replacing a part of the film with an ultraviolet-cut transparent film, and hermetically preserving the dried body covered with the film, if necessary.

15. The method of quickly drying a fresh sample according to claim 1, wherein the dried body is preserved in a space in which a deoxidizing agent and/or a drying agent is contained.

16. The method of quickly drying a fresh sample according to claim 1, wherein the dried body is fixed to a space which is sealed by an ultraviolet-cut transparent resin at least on one side thereof, and a deoxidizing agent and/or a drying agent is introduced into the space.

17. The method of quickly drying a fresh sample according to claim 1, wherein the surface of the dried body has an ultraviolet-cut aqueous solution applied thereto.

18. A dried body of a fresh sample, which maintains the color and smell of the fresh sample in nature and without deformation.

19. The dried body of claim 18, the surface of which has an ultraviolet-cut aqueous solution applied thereto.

20. A kit for quickly drying a fresh sample comprising a moisture absorbent porous flexible sheet which covers a fresh sample to be dried, silica gels which surrounds the fresh sample covered with the moisture absorbent porous flexible sheet, and a heat-resistant container to which a microwave is permeable and in which the fresh sample to be dried covered by the moisture absorbent porous flexible sheet and surrounded by silica gels are placed, wherein the moisture absorbent porous flexible sheet has a size in which a part of the sheet extends out of the container.

* * * * *